(12) United States Patent
Yacoubian

(10) Patent No.: US 10,441,255 B2
(45) Date of Patent: Oct. 15, 2019

(54) MULTIPLE PURPOSE SURGICAL INSTRUMENTS

(71) Applicant: Stephan V. Yacoubian, Burbank, CA (US)

(72) Inventor: Stephan V. Yacoubian, Burbank, CA (US)

( * ) Notice: Subject to any disclaimer, the term of this patent is extended or adjusted under 35 U.S.C. 154(b) by 126 days.

(21) Appl. No.: 15/180,861

(22) Filed: Jun. 13, 2016

(65) Prior Publication Data

US 2016/0278751 A1  Sep. 29, 2016

Related U.S. Application Data

(63) Continuation of application No. 13/227,247, filed on Sep. 7, 2011, now Pat. No. 9,364,248.

(60) Provisional application No. 61/380,623, filed on Sep. 7, 2010.

(51) Int. Cl.
| | | |
|---|---|---|
| *A61B 17/00* | (2006.01) | |
| *A61B 17/32* | (2006.01) | |
| *A61B 90/00* | (2016.01) | |
| *A61B 1/06* | (2006.01) | |
| *A61B 1/313* | (2006.01) | |
| *A61B 1/317* | (2006.01) | |
| *A61B 5/107* | (2006.01) | |
| *A61B 17/17* | (2006.01) | |
| *A61B 18/00* | (2006.01) | |

(52) U.S. Cl.
CPC ......... *A61B 17/00234* (2013.01); *A61B 1/06* (2013.01); *A61B 1/317* (2013.01); *A61B 1/3132* (2013.01); *A61B 5/1075* (2013.01); *A61B 17/1703* (2013.01); *A61B 17/32002* (2013.01); *A61B 90/06* (2016.02); *A61B 2017/00353* (2013.01); *A61B 2017/320024* (2013.01); *A61B 2018/00577* (2013.01); *A61B 2090/061* (2016.02); *A61B 2090/3618* (2016.02)

(58) Field of Classification Search
CPC .............. A61B 17/00234; A61B 34/30; A61B 1/00096; A61B 1/00156; A61B 1/00135; A61B 1/00101
See application file for complete search history.

(56) References Cited

U.S. PATENT DOCUMENTS

| | | | | |
|---|---|---|---|---|
| 5,184,602 A | * | 2/1993 | Anapliotis | A61B 1/00135 600/131 |
| 6,887,196 B2 | * | 5/2005 | Arai | A61B 1/00101 600/170 |
| 2009/0048483 A1 | * | 2/2009 | Yamamoto | A61B 1/00156 600/109 |
| 2009/0312608 A1 | * | 12/2009 | Wallace | A61B 1/00096 600/160 |
| 2010/0168763 A1 | * | 7/2010 | Zhao | A61B 34/30 606/130 |

* cited by examiner

*Primary Examiner* — Carl H Layno
*Assistant Examiner* — Dacheng Xie
(74) *Attorney, Agent, or Firm* — Polsinelli PC; Adam C. Rehm

(57) ABSTRACT

A multiple-purpose surgical instrument having a reflecting, rendering, and sizing tool to increase visibility and provide three-dimensional depth perception of a surgical site so that realization of a condition of the surgical site and safety are enhanced during an arthroscopic or laparoscopic procedure.

20 Claims, 9 Drawing Sheets

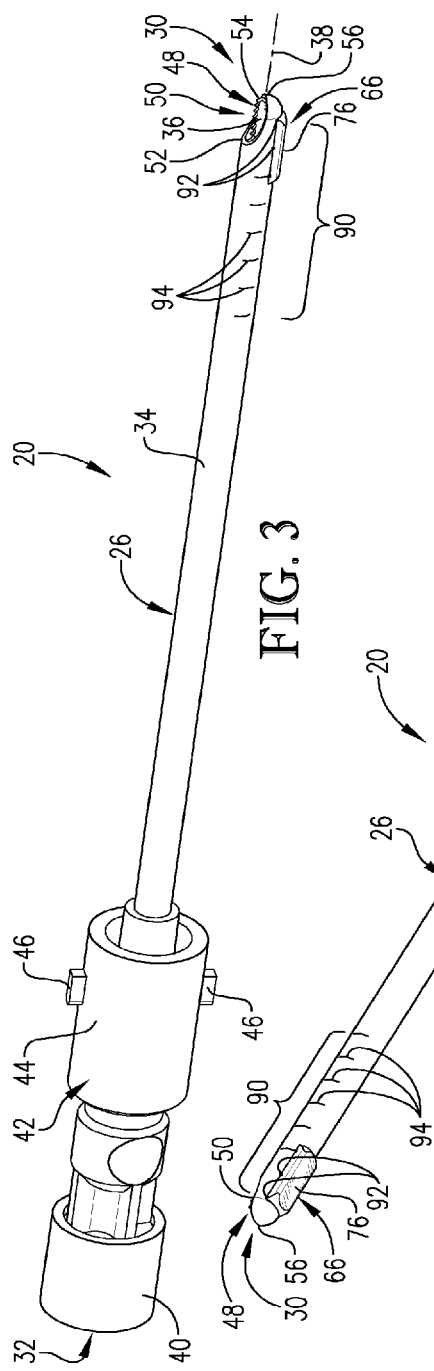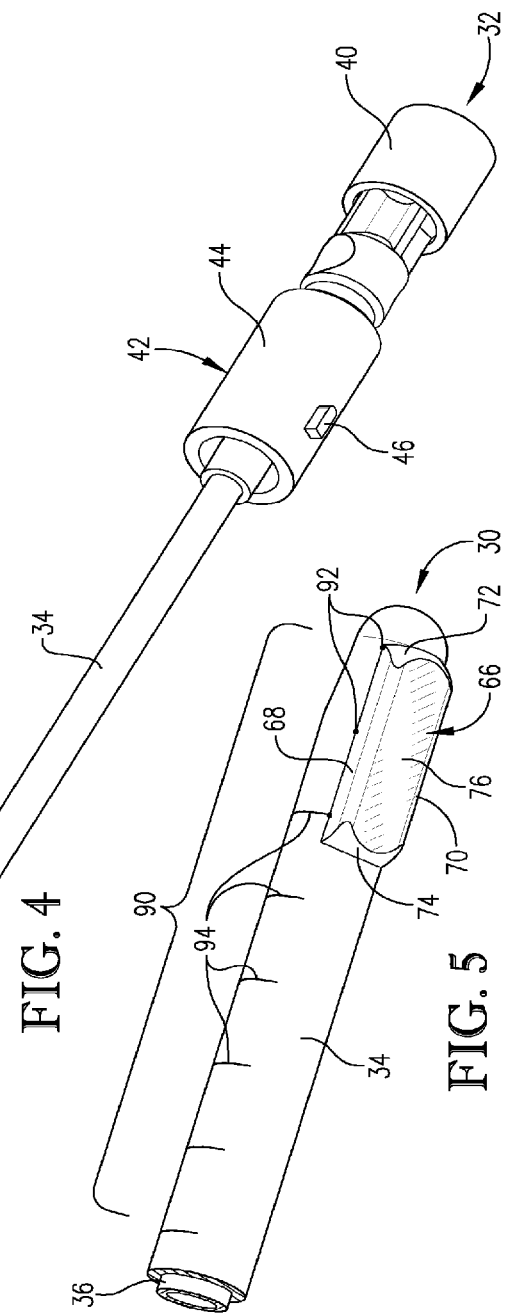

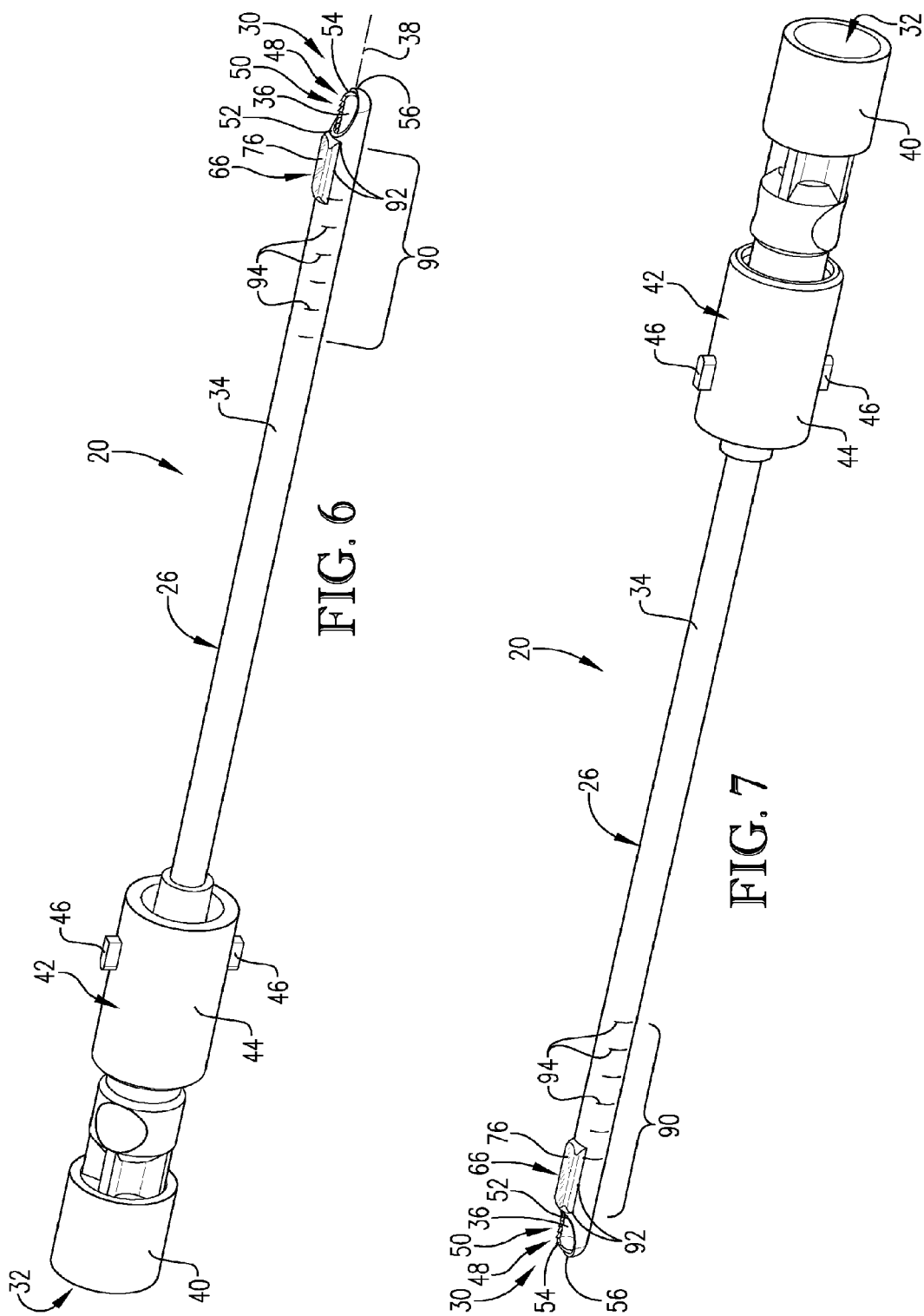

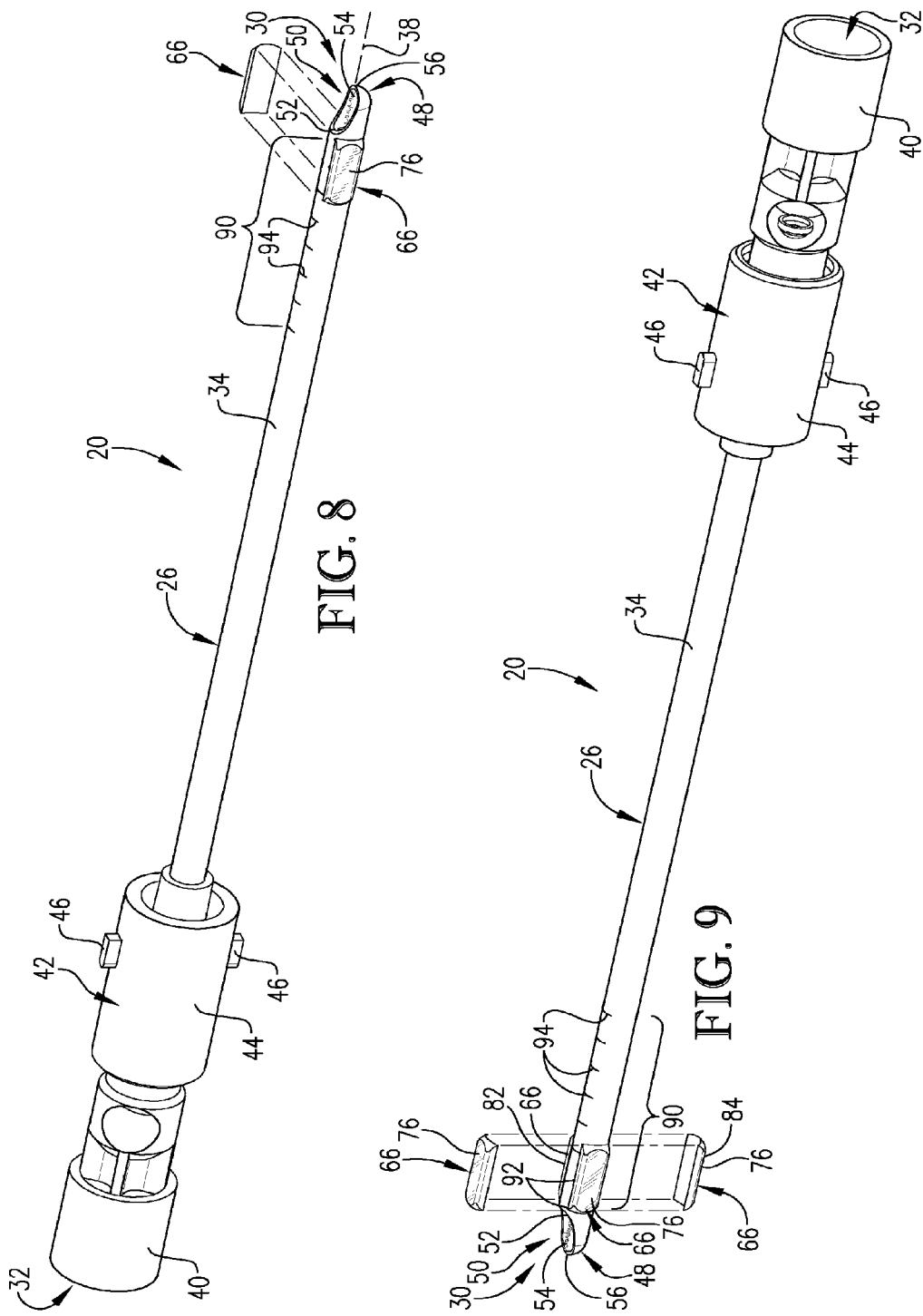

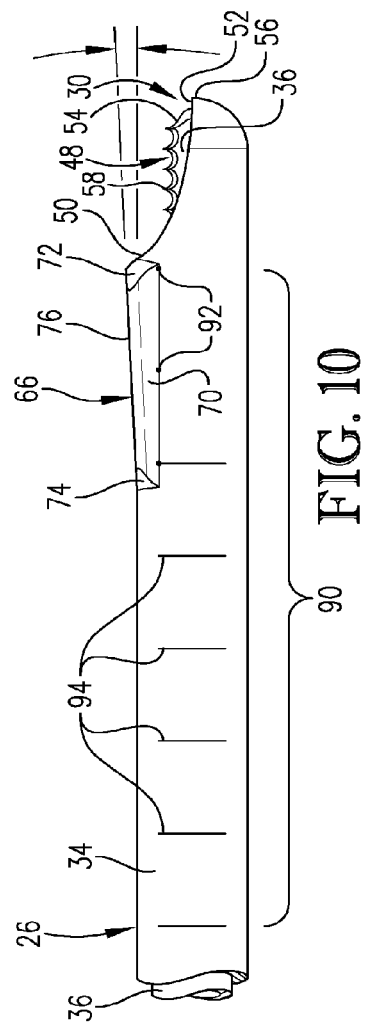
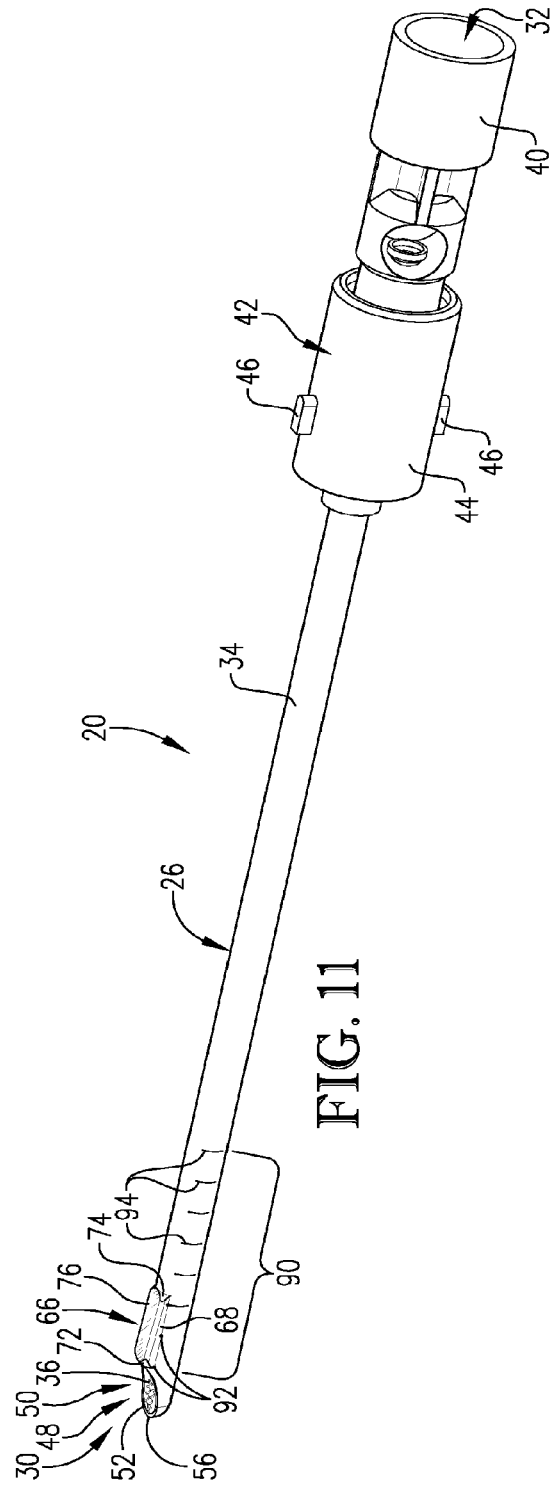

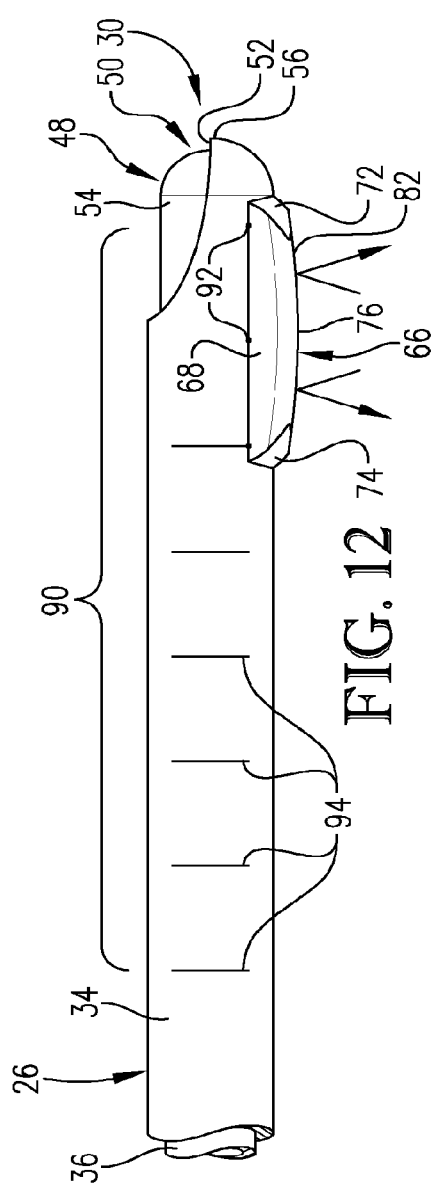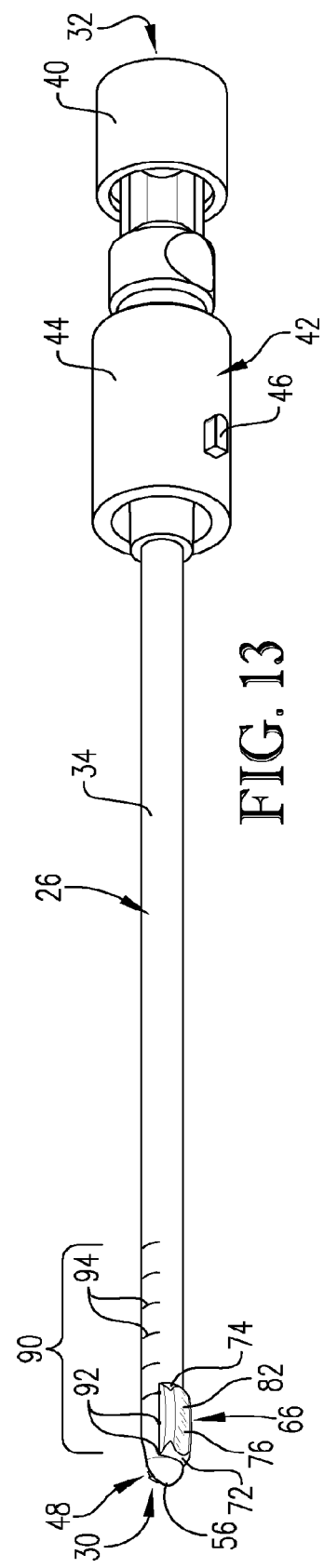
FIG. 12
FIG. 13

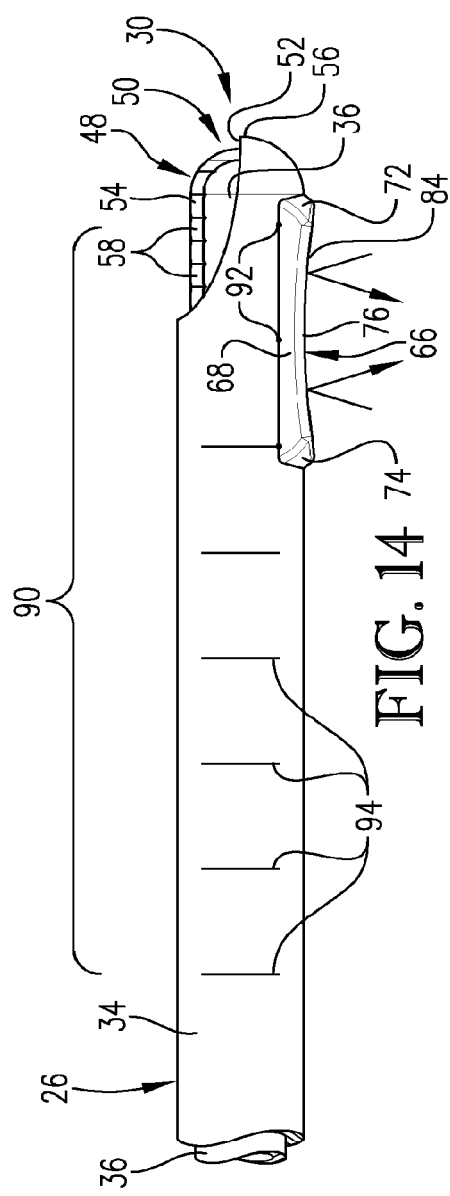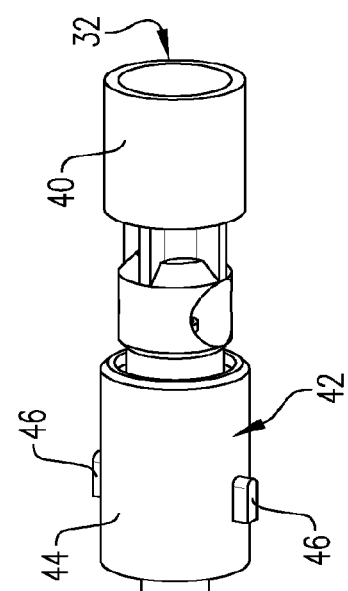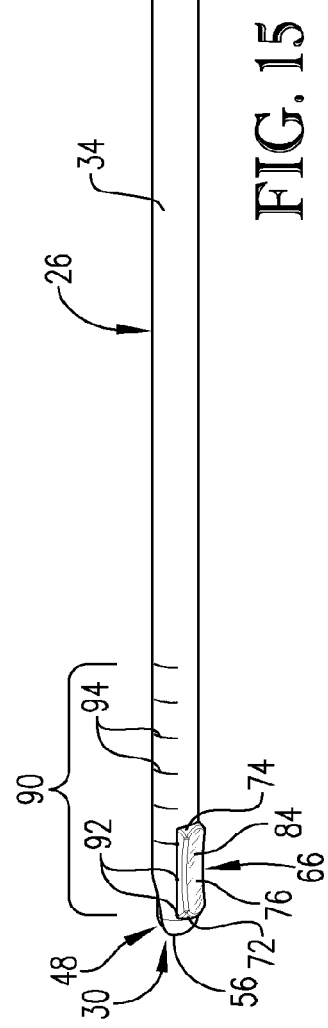
FIG. 14
FIG. 15

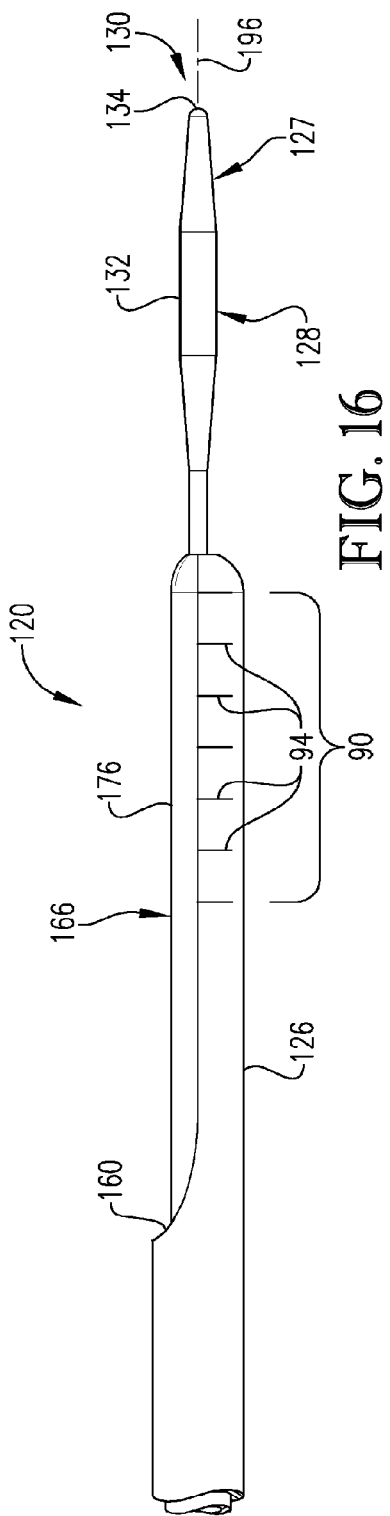
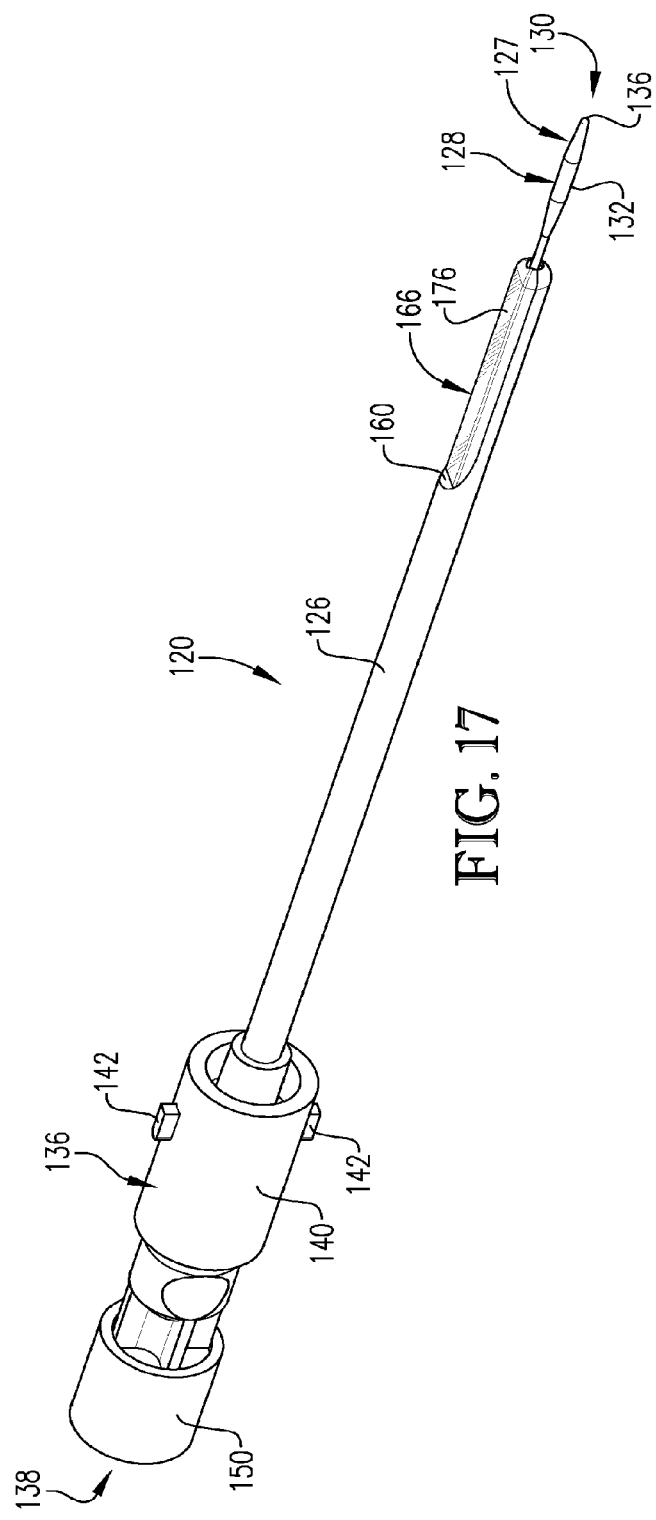

MULTIPLE PURPOSE SURGICAL INSTRUMENTS

CROSS-REFERENCE TO RELATED APPLICATION

This Patent Application claims priority to U.S. Patent Application Ser. No. 61/380,623 filed Sep. 7, 2010 and issued as U.S. Pat. No. 9,364,248 and U.S. patent application Ser. No. 13/227,247 filed Sep. 7, 2011, the entire contents of which are herein incorporated by reference in their entireties.

BACKGROUND OF THE INVENTION

1. Field of the Invention

The present inventive concept relates generally to medical instruments, and more particularly, to surgical instruments having a multi-purpose tool positioned at a distal end thereof operable to reflect, render, and size a surgical site so that visibility and safety are enhanced during an arthroscopic or laparoscopic surgical procedure.

2. Description of the Related Art

Arthroscopic surgery is a minimally invasive surgical procedure during which an interior portion of the human body, for example an interior of a joint, is examined or operated on using an arthroscope. An arthroscope is a type of endoscope or miniature camera operable to be inserted into the joint via a small incision to enable a surgeon to view the joint and perform a surgical operation without fully opening the joint. Although arthroscopic procedures may be performed on virtually any part of the human body, joints of the wrist, elbow, shoulder, hip, knee, ankle, and foot are most commonly examined and operated on.

During general arthroscopic procedures, the surgeon is required to make as few as two incisions to perform an arthroscopic examination or an arthroscopic operation. In such procedures, the surgeon may examine the joint to make a diagnosis by making an incision and inserting the arthroscope, which transmits a real-time image of the joint area to a video monitor. In this manner, the surgeon is able to diagnose, for example, torn joint tissue such as ligaments and menisci or cartilage. To perform an arthroscopic operation, the surgeon may make another incision adjacent to the arthroscope and insert a surgical instrument to be used in coordination with the arthroscope. In this manner, the surgeon is able to perform the operation to, for example, repair torn joint tissue. Although undesirable, it may be necessary for the surgeon to make additional incisions for the arthroscope and/or surgical instrument to, for instance, obtain another perspective of a joint.

Surgical instruments used in arthroscopic surgery are elongated and smaller than traditional surgical instruments, have a distal-working end to perform a function, such as proving, shaving, and drilling, and may be connected to a drive motor with a power source. While some arthroscopic surgical instruments, such as a probe, do not require power, other instruments, such as a shaver, are usually connected to a drive motor with power source. Power sources are generally electric or pneumatic and, upon connection of the instrument to the drive motor, permit a portion of the instrument to be driven, for example, in an oscillating or reciprocating manner.

Conventional shavers generally include an inner-rotatable shaft that is substantially enclosed by an outer-stationary shaft. A window at a distal end of the outer-stationary shaft exposes a toothed end of the inner-rotatable shaft, which defines a working end of the shaver. A conventional arthroscopic shaver is disclosed in U.S. Patent Publication No. 2006/0259055 to Thorne, the entire contents of which is herein incorporated by reference in its entirety.

Although conventional arthroscopic instruments and techniques have generally improved over time, such still suffer from various limitations. For instance, area surrounding and along a joint is extremely confined, which limits visibility of the joint. If the surgeon is unable to adequately view the joint via the arthroscope, the surgeon may decide to withdraw the arthroscope, make another incision, and reinsert the arthroscope to obtain a better perspective of the joint. Such is undesirable for at least the reasons that additional incisions and/or manipulation of the arthroscope and surgical instruments increase trauma to a patient, lengthen the time period required of the surgical procedure, which elevate the risks associated with the surgical procedure. Often times, surgeons will forego a complete inspection of a joint to avoid making any additional incisions or minimize manipulations, which may cause an injury to the joint, such as a tear, to be left untreated.

An additional limitation of conventional arthroscopic instruments and techniques relate to the inherent two-dimensional nature of real-time images displayed by video monitors during an arthroscopic procedure. Without a third dimension, the surgeon may be unable to fully realize a depth of an object displayed by the video monitor, which may result in an incorrect diagnosis of a joint during an arthroscopic examination or less precise treatment of a joint during an arthroscopic operation.

Accordingly, there is a need for arthroscopic instruments that do not suffer from the limitations of conventional arthroscopic instruments, increase visibility, realization, and safety during use thereof, are versatile to permit use in a wide variety of applications, have a simple design that is easy to use, and does not prolong recovery time or expenses of a patient.

SUMMARY OF THE INVENTION

The following brief description is provided to indicate the nature of the subject matter disclosed herein. While certain aspects of the present inventive concept are described below, the summary is not intended to limit the scope of the present inventive concept. Embodiments of the present inventive concept provide an inventive concept for medical instruments, a method of manufacture such medical instruments, and a method of using such medical instruments in arthroscopic and laparoscopic procedures. The present inventive concept does not suffer from and remedies the deficiencies of conventional devices such as those previously set forth herein.

The present inventive concept provides, in its simplest form, a medical surgical instrument having a reflecting, rendering, and sizing tool positioned at a distal end thereof, which is operable to reflect, render, and size a surgical site so that visibility and safety are enhanced when the instrument is used during an arthroscopic and/or laparoscopic surgical operation. The medical instrument may be one or more of a plurality of designs to provide one or more of a plurality of functions. That the present inventive concept provides increased design elements with increased functionality relative to conventional medical instruments.

An object of the present inventive concept is to provide an arthroscopic medical instrument having a plurality of reflective surfaces, e.g., four with differing functionality relative to each other, e.g., degrees of reflectivity, shape or configuration (concave, convex, domed, inversely domed, flat or planar), that are operable to provide different degrees of visibility in and/or of a patient, e.g., a joint, that is reflected from the reflective surface and/or light that is transmitted to the patient that is reflected from the reflective surface.

Another object of the general inventive concept is to increase the functionality of conventional medical instruments such as arthroscopic medical instruments including arthroscopic shavers, ablators, burrs, and biters by providing reflective surfaces on such medical instruments, and to consequently increase the efficiency and safety of conventional medical techniques that utilize these medical instruments.

Another object of the general inventive concept is to provide arthroscopic medical instruments that are easy to use, comparatively simple to manufacture, and especially well adapted for the intended usage thereof.

The aforementioned objects and advantages of the present inventive concept may be achieved by providing a multi-function medical instrument having a plurality of tools for performing various surgical procedures on a surgical site. The multi-function medical instrument may include an elongated body having a handling end and a working end opposite the handling end, a handle at least partially defining the handling end of the elongated body, the handle having a gripping surface, a surgical procedure tool at least partially defining the working end of the elongated body, the surgical procedure tool operable to perform a surgical operation on the surgical site, and/or a realization tool positioned along the elongated body and substantially adjacent to the working end of the elongated body, the realization tool operable to permit a surgical examination on the surgical site.

The realization tool may include at least one realization tool positioned along the elongated body so that the realization tool is accessible relative to the surgical procedure tool by one or more of (i) changing an angle of the elongated body relative to the surgical site, (ii) laterally shifting the elongated body relative to the surgical site, (iii) changing an angle of the elongated body relative to the surgical site and laterally shifting the elongated body relative to the surgical site, (iii) laterally shifting the elongated body and rotating the elongated body 90° relative to the surgical site, (iv) laterally shifting the elongated body and rotating the elongated body 180° relative to the surgical site, and/or (v) laterally shifting the elongated body and rotating the elongated body 270° relative to the surgical site. The realization tool may be at least partially or completely embedded within the elongated body and have a recessed portion spacing a portion of the elongated body from a portion of the realization tool. The realization tool may include a plurality of realization tools. Each one of the realization tools may have one or more surfaces with a same degree of reflectivity or with different degrees of reflectivity operable to reflectively transmit (i) an image of the surgical site with rendering or non-rendering, and/or (ii) a beam of light to the surgical site with rendering or non-rendering. One or more of the plurality of realization tools may be positioned equidistant from a tip of the working end of the elongated body, longitudinally about the elongated body, and/or circumferentially about the elongated body.

Each of the surfaces of the plurality of realization tools may have a different and/or same degree of reflectivity operable to render the image of the surgical site or the beam of light to the surgical site with varying degrees of clarity. Each of the surfaces of the plurality of realization tools may have a respective surface configuration operable to render the image of the surgical site to be magnified and/or minimized and render the beam of light to the surgical site to be focused and/or scattered. Each configuration may include at least one or more of a convex surface and/or a concave surface.

The multi-function medical instrument may include a scale with units of measurement. The scale may be operable to permit sizing of an image reflectively transmitted by one of the plurality of realization tools. The scale may be circumferentially and/or longitudinally positioned on the elongated body and/or adjacent to one or more of the plurality of realization tools. The scale may be accessible with respect to the surgical operation tool by (i) laterally shifting the elongated body relative to the surgical site, or (ii) laterally shifting the elongated body and rotating the elongated body 45° relative to the surgical site. The scale may be accessible with respect to the realization tool by rotating the elongated body between 1° and 45° relative to the surgical site.

The aforementioned objects and advantages of the present inventive concept may further be achieved by providing a medical instrument for performing a surgical procedure on a surgical site. The medical instrument may include an elongated body, a handle at least partially defining a handling end of the elongated body, the handle having a gripping surface, a surgical operation or procedure tool at least partially defining a working end of the elongated body, the working end of the elongated body being opposite to the handling end of the elongated body, the surgical procedure tool operable to perform a surgical function or manipulation on the surgical site, and/or a realization tool positioned along the elongated body and substantially adjacent to the realization tool. The realization tool may be operable to reflectively transmit (i) an image of the surgical site in a rendered and/or a non-rendered manner, (ii) a beam of light to the surgical site in a rendered and/or a non-rendered manner, or (iii) both. The realization tool may be accessible after use of the surgical procedure tool; that is, when the surgical procedure tool is oriented in a use position, by (i) rotating the elongated body relative to the surgical site, (ii) laterally shifting the elongated body relative to the surgical site, and/or (iii) both.

The realization tool may be accessible after use of the surgical procedure tool, that is, when the surgical procedure tool is oriented in a use position, by rotating the elongated body 180°. The realization tool may be accessible after use of the surgical procedure tool, that is, when the surgical procedure tool is oriented in a use position, by laterally shifting and rotating the elongated body 180°. The realization tool may include a plurality of realization tools that are individually and/or sequentially accessible with respect to the surgical procedure tool, that is, when the surgical procedure tool is oriented in a use position, by (i) laterally shifting the elongated body, (ii) laterally shifting the elongated body and rotating the elongated body 90°, (iii) laterally shifting the elongated body and rotating the elongated body 180°, and/or (iv) laterally shifting the elongated body and rotating the elongated body 270°.

The plurality of realization tools may be positioned equidistant from a tip of the working end of the elongated body or at various differing positions from the tip of the working end. The realization tool may have a degree of reflectivity operable to render the image of the surgical site and/or the beam of light to the surgical site with increased, decreased, and/or unchanged clarity, spread, or convergence. The realization tool may include a plurality of realization tools having same or different degrees of reflectivity to independently render the image of the surgical site or the beam of light to the surgical site with increased, decreased, and/or unchanged clarity, spread, or convergence.

The realization tool may have a configuration operable to render the image of the surgical site to be magnified and/or minimized or the beam of light to the surgical site to be focused and/or scattered. The configuration of the realization tool may include at least one of a convex surface operable to spread light beams and/or a concave surface operable to converge light beams. The realization tool may include a plurality of realization tools having a respective configuration operable to render the image of the surgical site to be magnified and/or minimized or the beam of light to the surgical site to be focused and/or scattered. Each configuration may include at least one of a convex surface operable to spread light beams and/or a concave surface operable to converge light beams. The realization tool may have one or more of a plurality of reflective surfaces that are variably angled with respect to each other and/or are parallel to or angled relative to an axis defined by the elongated body.

The medical instrument may also include one or more scales with the same or different units of measurement. The scale(s) may be operable to permit sizing of an image reflectively transmitted by the realization tool. The scale(s) may be circumferentially and/or longitudinally positioned on the elongated body and/or adjacent to the realization tool. The realization tool may be further operable to perform a dimensioning function. The dimensioning function may provide a basis for a third dimension when the medical instrument is utilized with an arthroscope and/or a video monitor having a two-dimensional display. The surgical manipulation performed by the surgical tool may be a physical manipulation of a part of the surgical site; the physical manipulation being one of probing, shaving, ablating, burring, and biting. The realization tool may not be operable to physically manipulate the surgical site.

The foregoing and other objects are intended to be illustrative of the present inventive concept and are not meant in a limiting sense. Many possible embodiments of the present inventive concept may be made and will be readily evident upon a study of the following specification and accompanying drawings comprising a part thereof. Various features and subcombinations of present inventive concept may be employed without reference to other features and subcombinations. Other objects and advantages of this present inventive concept will become apparent from the following description taken in connection with the accompanying drawings, wherein is set forth by way of illustration and example, an embodiment of this present inventive concept and various features thereof.

BRIEF DESCRIPTION OF THE DRAWINGS

A preferred embodiment of the invention, illustrative of the best mode in which the applicant has contemplated applying the principles, is set forth in the following description and is shown in the drawings.

FIG. 3 is a right side perspective view of the medical instrument illustrated in FIG. 1;

FIG. 4 is a left side perspective view of the medical instrument illustrated in FIG. 1;

FIG. 5 is a magnified bottom perspective view of the medical instrument illustrated in FIG. 1;

FIG. 6 is a right side perspective view of the medical instrument illustrated in FIG. 1, illustrating an alternate configuration of the realization tool;

FIG. 7 is a left side perspective view of the medical instrument illustrated in FIG. 6;

FIG. 8 is a right side perspective view of the medical instrument illustrated in FIG. 1, illustrating an alternate configuration of a plurality of realization tools with one of the realization tools exploded from the medical instrument;

FIG. 9 is a left side perspective view of the medical instrument illustrated in FIG. 1, illustrating an alternate configuration of a plurality of realization tools with two of the realization tools exploded from the medical instrument;

FIG. 10 is a magnified right side perspective view of the medical instrument illustrated in FIG. 1, illustrating an angled surface of the realization tool;

FIG. 11 is a left side perspective view of the medical instrument illustrated in FIG. 10;

FIG. 12 is a magnified right side perspective view of the medical instrument illustrated in FIG. 1, illustrating a convex surface of the realization tool;

FIG. 13 is a left side perspective view of the medical instrument illustrated in FIG. 12;

FIG. 14 is a magnified right side perspective view of the medical instrument illustrated in FIG. 1, illustrating a concave surface of the realization tool;

FIG. 15 is a left side perspective view of the medical instrument illustrated in FIG. 14;

FIG. 16 is a right side view of an alternative medical instrument; and

FIG. 17 is a right side perspective view of the medical instrument illustrated in FIG. 16.

DETAILED DESCRIPTION OF THE PREFERRED EMBODIMENTS

The following detailed description of the present inventive concept references the accompanying drawings that illustrate specific embodiments in which the present inventive concept can be practiced. The embodiments are intended to describe aspects of the present inventive concept in sufficient detail to enable those skilled in the art to practice the present inventive concept. Other embodiments can be utilized and changes can be made without departing from the scope of the present inventive concept. The following detailed description is, therefore, not to be taken in a limiting sense. The scope of the present inventive concept is defined only by the appended claims, along with the full scope of equivalents to which such claims are entitled.

In this description, references to "one embodiment," "an embodiment," or "embodiments," mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, or the like described in one embodiment may also be included in other embodiments, but is not necessarily included. Thus, the present technology can include a variety of combinations and/or integrations of the embodiments described herein.

Figure 1:
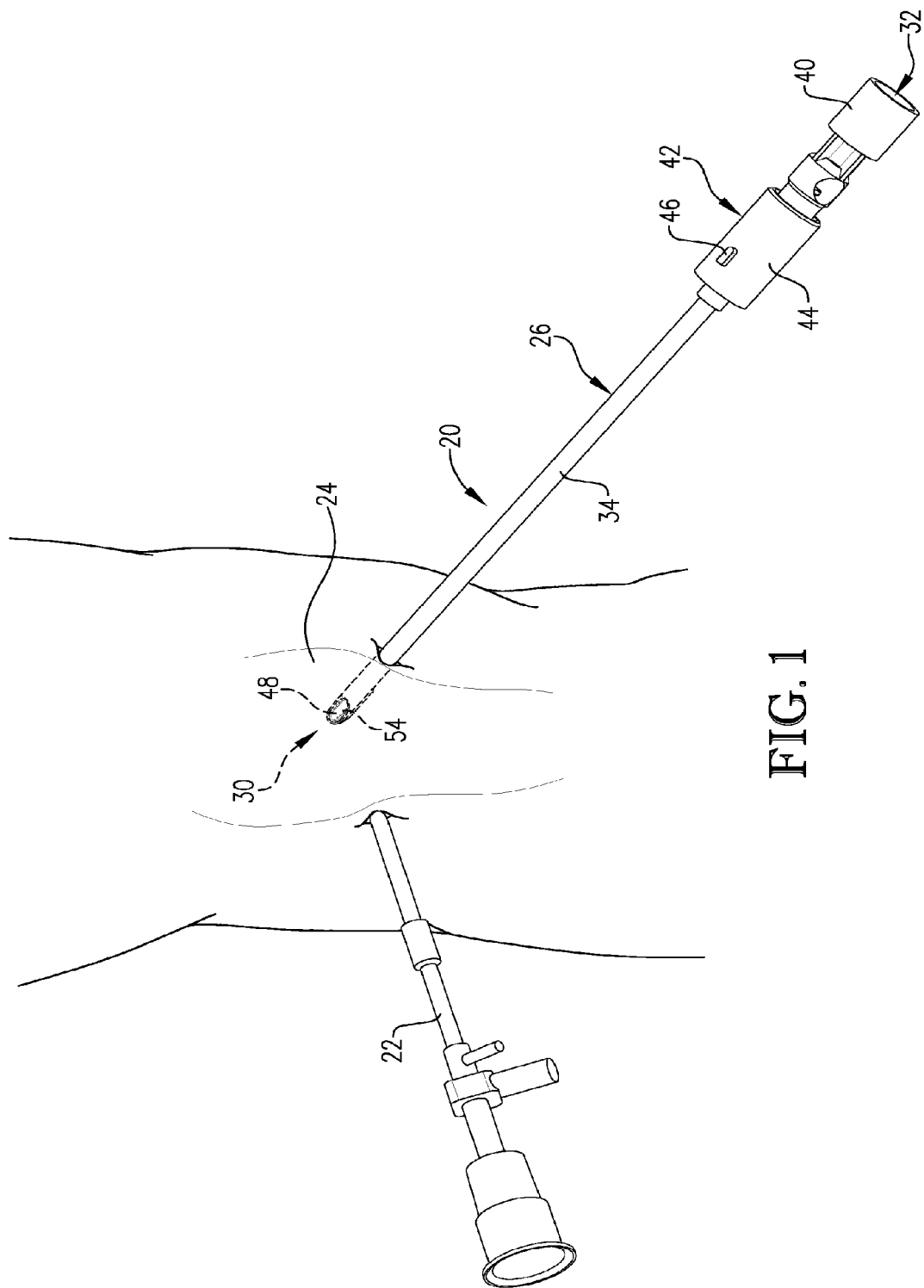
FIG. 1 is a perspective view of an arthroscopic procedure of a knee joint with an arthroscope and an arthroscopic medical instrument each inserted into the knee joint via an incision, illustrating a surgical tool of the medical instrument in a use position with the surgical tool oriented to perform a manipulation on a portion of the knee joint.
Figure 2:
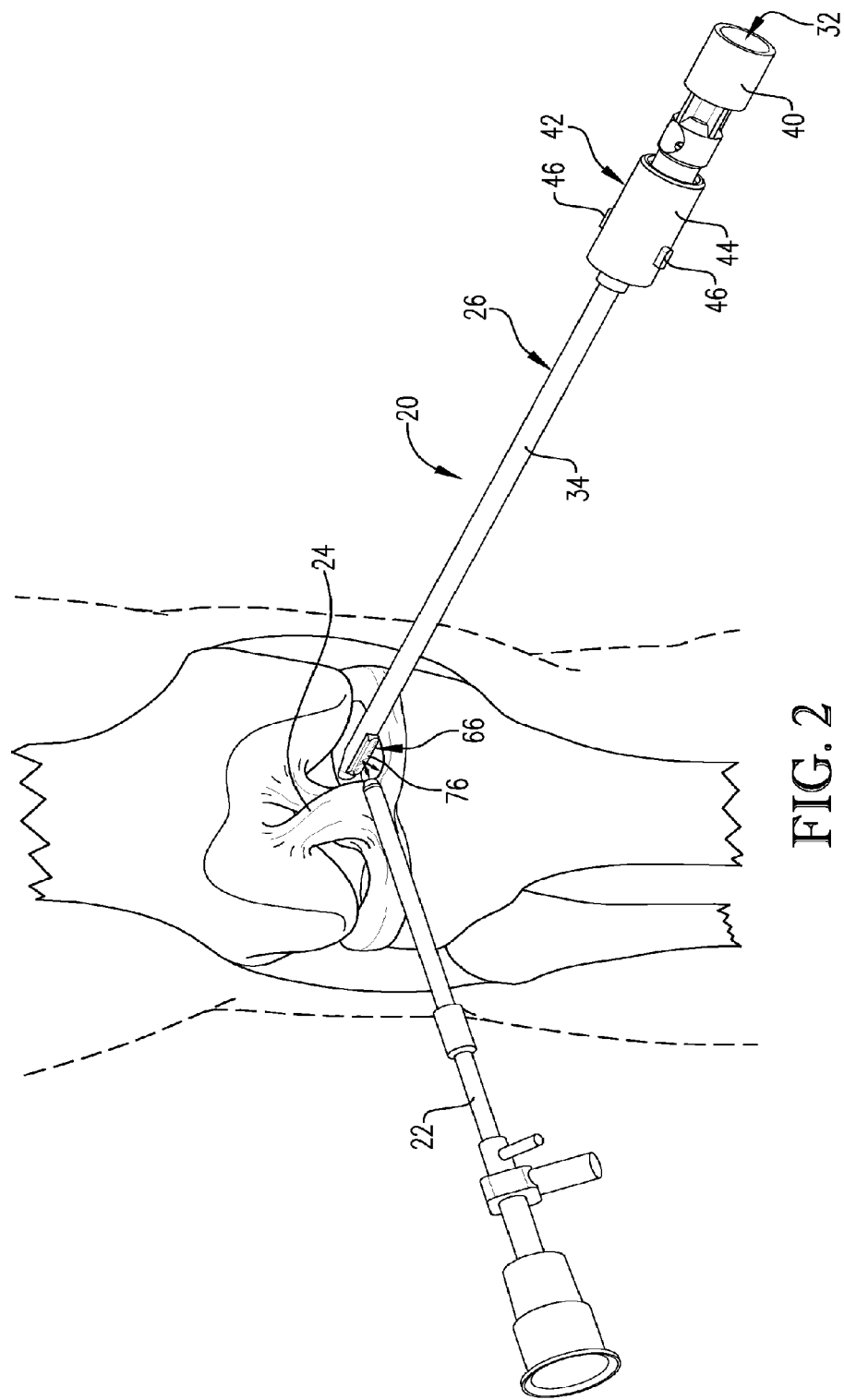
FIG. 2 is a perspective view of an interior of the knee joint illustrated in FIG. 1, illustrating a realization tool of the medical instrument in a use position with the medical instrument oriented to reflectively transmit an image of a portion of the knee joint to the arthroscope for viewing via the realization tool and light emitted from the arthroscope to the portion of the knee joint.

Turning to the drawings and particularly FIGS. 1 and 2, a surgical or medical instrument 20 is illustrated with an arthroscope 22 during use by a surgeon in arthroscopic surgery. For illustrative purposes, the medical instrument 20 is designed to function as, among other things, a shaver and is illustrated in use with a knee joint 24. It is foreseen, however, that the arthroscopic instrument 20 could be designed to provide any one or more of a plurality of functions and is not limited to a shaver. For instance, the arthroscopic instrument 20 could be a probe, ablator, burr, biter and/or the like, and/or be designed to saw, probe, suction, and/or the like with deviating from the scope of the present inventive concept. It is further foreseen that the medical instrument 20 could be used to perform an arthroscopic operation, a general surgery such as a laparoscopic or cholycystectomy operation, or any other type of operation on any one or more parts of the human or animal body and is not limited to use with the knee joint 24. For instance, the medical instrument 20 could be used to perform a surgical operation on joints of the wrist, elbow, shoulder, hip, knee, foot, and/or the like without deviating from the scope of the present inventive concept. The arthroscope 22 is a conventional arthroscope such as that disclosed in U.S. Pat. No. 6,110,105 to Durell, the entire contents of which is herein incorporated by reference in its entirety.

The medical instrument 20 has an elongated body 26 and includes a working end 30 at a distal end of the medical instrument 20 and a handling end 32 at a proximal end that is opposite to the working end 30. The body 26 includes a longitudinally-extending stationary outer shaft 34 that houses and substantially encloses a movable inner shaft 36, as illustrated in FIGS. 3-11. The shafts 34, 36 have a common axis 38 that runs parallel to the elongated body 26. In the exemplary embodiment, the inner shaft 36 is operable to oscillate with respect to the outer shaft 34 about the axis 38, but it is foreseen that the inner shaft 36 could be operable to travel in other manners relative to the outer shaft 34, such as pivoting, without deviating from the scope of the present inventive concept.

The inner shaft 36 is secured to a driven end 40 that protrudes through a handle 42 secured to the outer shaft 34. The driven end 40 and the handle 42 cooperatively define the handling end 32 of the medical instrument 20. The driven end 40 is sized and shaped to securely mate with a drive motor and a power source so that the inner shaft 36 may be driven or oscillated with respect to the outer shaft 34 at high speeds. The handle 42 provides a gripping surface 44 with a plurality of laterally-protruding nubs 46 operable to facilitate secure handling of the medical instrument 20 by the surgeon.

At and defining the working end 30 of the medical instrument 20 is a tool 48 operable to perform a function. For illustrative purposes, the tool 48 performs a shaving function and includes a cutting window 50 with a perimeter edge 52 situated in and along the outer shaft 36 of the surgical instrument. In the exemplary embodiment, the window 50 and particularly the perimeter edge 52 thereof extends from a top of the outer shaft 36 to a middle of the outer shaft 36 and at a tip 56 of the medical instrument 20 to expose a cutting portion 54 of the inner shaft 36. It is foreseen, however, that the window 50 may be of any size and/or shape without deviating from the scope of the present inventive concept. In this manner, the window 50 is operable to permit a portion of the cutting portion 54 to extend past the perimeter edge 52 and out of the window 50 as the inner shaft 36 oscillates about the axis 38. Thus, the cutting portion 52 is operable to abut and penetrate into or shave a surface at a surgical site when such a surface is placed in and/or adjacent to the window 50. A plurality of teeth 58 are provided to facilitating shaving, as best illustrated by FIG. 10. As previously discussed, the tool 48 of the medical instrument 20 and functionality thereof is not limited to shaving and the medical instrument 20 may be designed to perform any one or more of a plurality of functions, such as those performed by conventional arthroscopic instruments, without deviating from the scope of the present inventive concept.

Also at and defining the working end 30 of the medical instrument 20 is a multi-purpose realization tool 66 positioned on the outer shaft 34. The multi-purpose tool 66 is operable to increase the surgeon's knowledge of or realization of a surgical site by reflecting, rendering, dimensioning, and/or sizing a surgical site and/or a portion thereof, for instance, directly or indirectly via the arthroscope 22, when the medical instrument 20 is oriented with respect to the surgical site. Additionally, the multi-purpose tool 66 provides a basis for a third dimension when used during arthroscopic procedure and a two-dimensional video monitor. Thus, the multi-purpose tool 66 may be synonymously referenced herein as a reflecting, rendering, sizing, dimensioning, object-enhancing, realization, or visualization tool. The multi-purpose tool 66 includes parallel side surfaces 68, 70 parallel front and rear surfaces 72, 74 extending perpendicular to the surfaces 68, 70, and a joining surface 76 adjoining the surfaces 68, 70, 72, 74, as best illustrated by FIG. 5. The surfaces 68, 70, 72, 74, 76 collaboratively define the functionality of the multi-purpose tool 66.

The position of the multi-purpose tool 66 on the outer shaft 34 of the medical instrument 20 is variable relative to the tool 48 and is selected based on desired function of the medical instrument 20 and/or tool 48 by the surgeon. For instance, the multi-purpose tool 66 may be oriented on a side of the outer shaft 34 opposite to the window 50, as illustrated in FIGS. 3 and 4. Further, the multi-purpose tool 66 may be oriented on a side of the outer shaft 34 that is the same as that of the window 50, as illustrated in FIGS. 6 and 7. Still further, the multi-purpose tool 66 may be oriented on lateral sides of the outer shaft 34 with respect to the window 50, as illustrated in FIG. 8, and/or on all sides of the outer shaft 34, as illustrated in FIG. 9. Thus, it is foreseen that any one or more multi-purpose tools 66 may be positioned anywhere along the outer shaft 34 of the medical instrument 20 without deviating from the scope of the present inventive concept.

Regarding the reflecting functionality of the multi-purpose tool 66, the joining surface 76 has a degree of reflectivity operable to redirect or reflect an image of an area of interest to the arthroscope 22 for viewing by the surgeon. Unless otherwise indicated, the joining surface 76 is flat or planar to the axis 38. The image may be, for example, a part of the body to be examined and/or a surgical site to be operated on. The reflecting functionality may also be used to reflectively transmit light emitted from the arthroscope 22 or other source to the area of interest to, for example, cast an intense light beam on the area of interest to facilitate viewing by the surgeon. The degree of reflectivity of the joining surface 76 of the multi-purpose tool 66 is variable and is determined based on desired function of the medical instrument 20 and/or tool 48 by the surgeon. In the exemplary embodiment, the joining surface 76 provides a degree of reflectivity of >99%.

When the medical instrument 20 has a plurality of the multi-purpose tools 66, as illustrated by FIGS. 8 and 9, each of the plurality of the multi-purpose tools 66, and particularly the joining surface 76 thereof, have different degrees of reflectivity that are sequentially accessed by the surgeon when the medical instrument 20 is rotated 90°. Further, as the medical instrument 20 is rotated, each of the plurality of the multi-purpose tools 66 independently and sequentially provides a relatively decreasing degree of reflectivity with a first of the plurality of the multi-purpose tools 66 having a first degree of reflectivity that is perfectly clear, a second of the plurality of the multi-purpose tools 66 having a lesser degree of reflectivity relative to the first, a third of the plurality of the multi-purpose tools 66 having a lesser degree of reflectivity relative to the second, and a fourth of the plurality of the multi-purpose tools 66 having a lesser degree of reflectivity relative to the third. For instance, the plurality of the multi-purpose tools 66 may have degrees of reflectivity of >99%, 90%, 80%, and/or >79%. It is foreseen, however, that each of the plurality of the multi-purpose tools 66 may have the same degree of reflectivity without deviating from the scope of the present inventive concept.

In the exemplary embodiment, the surfaces 68, 70, 72, 74, 76 are made of the same material, such as polished metal, a mirror, and/or the like, but it is foreseen that any one or more of the surfaces 68, 70, 72, 74, 76 may be made of different and/or the same material(s) without deviating from the scope of the present inventive concept. The present general inventive concept may be applied to newly manufactured tools or retrofitted to conventional tools, for example, by machining a portion of an elongated shaft of a conventional tool to provide a flat surface and affixing a mirror thereto. Hand polishing or diamond lapping may be performed additionally or instead of to achieve a desired degree of reflectivity for each of the multi-purpose tools 66.

Regarding the rendering functionality of the multi-purpose tool 66, the joining surface 76 is configured in a shape operable to render the area of interest as desired by the surgeon, and reflectively transmit a rendered image to the arthroscope 22 for viewing by the surgeon to facilitate examination thereof and/or operation thereon. For example, the joining surface 76 may be of a configuration operable to facilitate viewing of the area of interest via angling the surface 76. FIGS. 10 and 11 illustrate angling of the joining surface 76 at 5° relative to the axis 38 so that the multi-purpose tool 66 is operable to cast an image of the area of interest away from the working end 20 and toward the surgeon at the handling end 32 of the medical instrument 20. It is foreseen that the joining surface 76 may be angled at any degree relative to the axis 38 or parallel therewith without deviating from the scope of the present inventive concept. Additionally, the joining surface 76 may be of a configuration operable respectively magnifying and/or minimizing an image of the area of interest via a convexity or a concavity formed in the joining surface 76. The rendering functionality may also be used to reflectively transmit light from a light source to the area of interest to. Depending on the configuration of the joining surface 76, such is operable to reflectively transmit a scattered light beam or beams, a focused light beam, and/or an unchanged light beam.

FIGS. 12 and 13 illustrate a convex surface 82 that is operable to reflectively transmit a magnified view of the area of interest to the arthroscope 22 and/or reflectively transmit scattered light from a light source to provide ambient light to the area of interest. The convex surface 82 renders or converts parallel beams of light, that is, the image of the area of interest and/or light received from a light source, to divergent beams, which respectively causes the magnification and/or light-scattering effect of the joining surface 76 with the convex surface 82. FIGS. 14 and 15 illustrate a concave surface 84 that is operable to reflectively transmit a minimized view of the area of interest to the arthroscope 22 and/or reflectively transmit focused light from a light source to provide an intensely-focused light to the area of interest. The concave surface 84 renders or converts parallel beams of light, that is, the image of the area of interest and/or light received from a light source, to convergent beams, which respectively causes the minimization and/or light-focusing effect of the joining surface 76 with the concave surface 84. The degree of convexity and/or degree of concavity is variable and is selected by the surgeon based on the desired function of the medical instrument 20. It is foreseen that the joining surface 76 may be flat or planar to reflect parallel beams of light, domed to reflectively scatter beams of light 360° therefrom, inversely domed to reflectively focus light from 360° to a focused beam of light 360°, and/or any combination thereof to render the area of interest as desired by the surgeon without deviating from the scope of the present inventive concept.

Regarding the sizing functionality of the multi-purpose tool 66, a scale 90 is provided along a portion of the outer shaft 34 that corresponds to and is relative to the joining surface 76 of the multi-purpose tool 66. The scale 90 includes a plurality of points 92 and hatch marks 94 that are equally spaced from each other in units along the scale 90 on the portion of the outer shaft 34. Each of the hatch marks 94 extend parallel to each other and perpendicular to the axis 38 of the shafts 32, 34. The points 92 and hatch marks 94 are operable to measure an object, surface area, and/or the like in a known unit or units of measurement. In the exemplary embodiment, the scale 90 is in millimeters and is located on both sides of the outer shaft 34 with each side operable to independently measure an object, surface area, and/or the like in millimeters. It is foreseen, however, that the scale 90 may be in any known unit of measurement such as centimeters, inches, and/or the like without deviating from the scope of the present inventive concept. It is also foreseen that the scale 90 may be in one unit of measurement, for instance millimeters, on a first side of the outer shaft 34 and another different unit of measurement, for instance centimeters, on a second side of the outer shaft 34 without deviating from the scope of the present inventive concept. It is also foreseen that the scale 90 may include numerical indicia next to each of the points 92 and/or hatch marks 94 to indicate units of measurement along the scale 90. For instance, the scale 90 may include numerical indicia "1" positioned along the scale 90 to indicate one unit of measurement, numerical indicia 2 positioned along the scale 90 to indicate two units of measurement, and so on without deviating from the scope of the present inventive concept. The scale 90 may extend partially or entirely along the outer shaft 34.

In the exemplary embodiment, the multi-purpose tool 66 is constructed with the surfaces 68, 70, 72, 74, 76 having the desired degree(s) of reflectivity and/or configuration, and then affixed to a machined support surface of the outer shaft 34 via an adhesive or the like. It is foreseen, however, that the multi-purpose tool 66 may be machined on one portion of the outer shaft 34 so that the multi-purpose tool 66 is of the same material as the outer shaft 34. The multi-purpose tool 66 may be affixed at varying or equal distances from the tip 56 of the medical instrument 20 relative to each other.

The medical instrument 20 may be configured to perform any one or more of a number of functions. Turning to FIGS. 16 and 17, an alternative embodiment of a medical instrument 120 is provided that incorporates features of the medical instrument 20 and is configured to perform as a probe. As previously discussed, the surgical instrument 120 could be designed to provide any one or more of a plurality of functions and is not limited to a probe. The surgical instrument 120 has an elongated body 126 and includes a tool 127 operable to perform a function at a working or distal end 130 of the surgical instrument 120. For illustrative purposes the tool 128 is an elongated probing element 128 operable to perform a probing function. The probing element 128 extends parallel to the body 126 and includes a buttress portion 132 that is a thickest portion of the probing element 128 and a rounded tip 132 that defines the outermost shape of the surgical instrument 120 at the distal end 130. As previously discussed, the tool 127 of the surgical instrument 120 and functionality thereof is not limited to probing and the surgical instrument 120 may be designed to perform any one or more of a plurality of functions, such as those performed by conventional arthroscopic instruments, without deviating from the scope of the present inventive concept.

A handle 136 is located opposite to the distal end 130 and at a proximal end 138 of the surgical instrument 120. The handle 136 provides a gripping surface 140 with a plurality of laterally-protruding nubs 142 operable to facilitate secure handling of the surgical instrument 120 by the surgeon. The handle 136 is secured to a driven end 150 that protrudes from the handle 136. The driven end 150 and the handle 136 cooperatively define the proximal end 138 of the medical instrument 120. The driven end 150 is sized and shaped to securely mate with a drive motor and a power source so that the medical instrument 120 may provide suction, illumination, and/or the like to the area of interest.

Nested in a recessed surface 160 of the body 126 adjacent to the probing element 128 is a multi-purpose tool 166 embedded in the body 126. The multi-purpose tool 166 is operable to reflect, render, and/or size the surgical site and/or portion thereof for the surgeon, for instance, directly or indirectly via the arthroscope 22, when the surgical instrument 120 is oriented with respect to the surgical site. The multi-purpose tool 166 includes a working surface 176 that defines the functionality of the multi-purpose tool 66.

The multi-purpose tool 166 is positioned on the body 126 of the surgical instrument 120 relative to the tool 127 and may be of a variable quantity selected based on desired function of the medical instrument 120 and/or tool 127 by the surgeon. For instance, it is foreseen that a plurality of the multi-purpose tools 166 may be positioned around the body 126 relative to the tool 127 without deviating from the scope of the present inventive concept. For example, two sets of the multi-purpose tools 166 may be positioned embedded in and about the outer shaft 34 with each set of the multi-purpose tools 166 positioned parallel to each other, similar to the multi-purpose tools 66 illustrated in FIG. 9. Thus, it is foreseen that any one or more multi-purpose tools 166 may be positioned anywhere along the body 126 of the surgical instrument 120 without deviating from the scope of the present inventive concept.

Similar to the multi-purpose tool 66 previously discussed, the multi-purpose tool 166 is of the same material and is operable to perform the same reflecting, rendering, and sizing functions as the multi-purpose tool 66. Likewise, the multi-purpose tool 166 and any additional multi-purpose tools 166 may be of different or the same degrees of reflectivity and/or configurations, for example, concave and/or convex, depending on desired functionality of the surgeon. A scale 190 is provided along a portion of the body 126 that corresponds to and is relative to the working surface 176 of the multi-purpose tool 166. The scale 190 includes a plurality of hatch marks 94 that are equally spaced from each other in units along the scale 190 on the portion of the body 126. Each of the hatch marks 194 extend parallel to each other and perpendicular to a longitudinal axis 196 defined by the body 126 and common to the probing element 128. The hatch marks 194 are operable to measure an object, surface area, and/or the like in a known unit or units of measurement.

As should be evident from the foregoing, the medical instrument 120 is substantially the same as the medical instrument 20 with the like-named tools and/or other elements of both instruments 20, 120 performing the same or substantially the same functions. Thus, any description and/or functionality of the like-named tools and/or other elements provided herein may be applied to both.

When the surgeon desires to perform an arthroscopic procedure, whether it be an examination or operation, the surgeon selects an medical instrument that includes the teachings of the present inventive concept, such as the medical instruments 20, 120. For purposes of describing use of the medical instruments 20, 120, the medical instrument 20 to perform a shaving function shall be used. Any medical instrument that includes the teachings of the present inventive concept may be used, such as the medical instruments 20, 120, and such may be used in substantially the same manner with the description of the instrument 20 applied to all of the other instruments including medical instrument 120.

The surgeon attaches the driven end 40 of the medical instrument 20 to a drive motor with a power source. Upon making incisions in a patient adjacent to the knee joint 24, the surgeon independently inserts a portion of the arthroscope 22 and the working end 30 of the medical instrument 20 into the incisions so that the portion of the arthroscope 22 and the working end 30 of the medical instrument 20 substantially converge on the knee joint 24.

With the arthroscope 22 activated and transmitting the real-time image to the video monitor, the surgeon is able to examine the area of interest on the knee joint 24 and view the working end 30 of the medical instrument 20 via the video monitor. To perform a surgical operation on the area of interest, for example, shaving of the knee joint 24, the surgeon activates the medical instrument 20 and applies the cutting portion 54 to the portion of the knee joint 24 to be shaved, as illustrated in FIG. 1. If the surgeon is having difficulty viewing the area of interest directly via the arthroscope 22, the surgeon rotates the medical instrument 20 so that the multi-purpose tool 66 reflects an image of the area of interest to the arthroscope 20 and/or transmits light to the area of interest from a light source, as illustrated in FIG. 2.

If the medical instrument 20 is equipped with a plurality of the multi-purpose tools 66 about the outer shaft 34 of the medical instrument 20 having different degrees of reflectivity and/or different configurations, as is the medical instrument 20 illustrated in FIG. 9, the surgeon selectively accesses one of the multi-purpose tools 66 by pivoting or shifting, for instance, laterally, and/or rotating the medical instrument 20 90°, 180° or 270° relative to the tool 48 or until reaching the selected one of the multi-purpose tools 66.

The plurality of multi-purpose tools 66 are sequentially accessed by each 90° rotation of the medical instrument 20.

If the surgeon desires to magnify the area of interest and/or transmit scattered light to the area of interest, the surgeon pivots, shifts, and/or rotates the medical instrument 20 90°, 180° or 270° relative to the tool 48 or until reaching the multi-purpose tool 66 with the convex surface 82 and orients such relative to the area of interest so that a magnified image of the area of interest is transmitted to the arthroscope 22. If the surgeon desires to minimize the area of interest or transmit focused light to the area of interest, the surgeon pivots, shifts, and/or rotates the medical instrument 20 90°, 180° or 270° relative to the tool 48 or until reaching the multi-purpose tool 66 with the concave surface 84 and orients such relative to the area of interest so that a minimized image of the area of interest is transmitted to the arthroscope 22. If the surgeon desires to increase clarity, for instance, to better view the area of interest, the surgeon pivots, shifts, and/or rotates the medical instrument 20 90°, 180° or 270° relative to the tool 48 until reaching the multi-purpose tool 66 having a higher degree of reflectivity. If the surgeon desires to decrease glare, for instance, if light is preventing the surgeon from clearly viewing the area of interest, the surgeon pivots, shifts, and/or rotates the medical instrument 20 90°, 180° or 270° relative to the tool 48 or until reaching the multi-purpose tool 66 having a lower degree of reflectivity.

In some cases, the surgeon may want to measure the area of interest and/or obtain more accurate dimensioning thereof. To do such, the surgeon positions the medical instrument 20 along the area of interest to be measured and references the scale 90 positioned along the outer shaft 34 to obtain a measurement of the area of interest, for instance, in millimeters. By aligning the medical instrument 20 with respect to the knee joint 24, for instance, in a direction that is transverse to a horizontal and/or vertical direction of the knee joint 24, the medical instrument 20 provides a basis for a third dimension, such as depth, of the knee joint 24, which is particularly advantageous if the video monitor is displaying the knee joint 24 via the arthroscope 22 in only two dimensions.

If the scale 90 is to be utilized in coordination with the multi-purpose tool 66, for instance, if viewing of the area of interest is impaired and the surgeon desires to increase visibility of the area of interest, the surgeon positions the multi-purpose tool 66 having the flat or regular joining surface 76 so that the area of interest is not minimized or magnified and references the scale 90 to obtain a measurement of the area of interest, for instance, in millimeters. If the medical instrument 20 has scales 90 of different units of measurement, the surgeon slightly rotates (e.g., between one and forty-five degrees) or otherwise orients the medical instrument 20 to utilize the desired units.

Accordingly, the present inventive concept provides increased visibility and complete realization of an object so that a condition of an object, including any defects thereof, may be diagnosed and treated. The present inventive concept may be fully used by shifting and/or rotating maneuvers and does not require retraction from a surgical site.

Having now described the features, discoveries and principles of the general inventive concept, the manner in which the general inventive concept is constructed and used, the characteristics of the construction, and advantageous, new and useful results obtained; the new and useful structures, devices, tools, elements, arrangements, parts and combinations, are set forth in the appended claims.

It is also to be understood that the following claims are intended to cover all of the generic and specific features of the general inventive concept herein described, and all statements of the scope of the general inventive concept which, as a matter of language, might be said to fall there between.

What is claimed is:

1. A multi-function medical instrument having a plurality of tools for performing various surgical procedures on a surgical site, the multi-function medical instrument comprising:
    an elongated body having a handling end and a working end opposite the handling end;
    a handle at least partially defining the handling end of the elongated body, the handle having a gripping surface;
    a surgical procedure tool at least partially defining the working end of the elongated body, the surgical procedure tool operable to perform a surgical operation on the surgical site; and
    a realization tool positioned along the elongated body and substantially adjacent to the working end of the elongated body, the realization tool operable to permit a surgical examination on the surgical site,
    wherein,
        the realization tool is accessible relative to the surgical procedure tool using the handle to (i) laterally shift the elongated body, (ii) change an angle of the elongated body, or (iii) laterally shift and change an angle of the elongated body relative to the surgical site, and
        the realization tool has a surface with a degree of reflectivity operable to reflectively transmit an image of the surgical site with rendering or non-rendering directly from the surgical and directly to a user of the realization tool, the surface operable to transmit a beam of light to the surgical site with rendering or non-rendering.

2. The multi-function medical instrument according to claim 1, wherein the surface of the realization tool has a configuration operable to render the image of the surgical site to be magnified or minimized and render the beam of light to the surgical site to be focused or scattered.

3. The multi-function medical instrument according to claim 2, wherein the configuration includes at least one of a convex surface or a concave surface.

4. The multi-function medical instrument according to claim 1, further comprising:
    a scale with units of measurement, the scale operable to permit sizing of an object and/or surface area, the scale positioned along a portion of the realization tool on the elongated body to enable the user to measure the image.

5. The multi-function medical instrument according to claim 1, wherein the realization tool is embedded in the elongated body.

6. A medical instrument for performing a surgical procedure on a surgical site, the medical instrument comprising:
    an elongated body;
    a handle at least partially defining a handling end of the elongated body, the handle having a gripping surface;
    a surgical operation tool at least partially defining a working end of the elongated body, the working end of the elongated body being opposite to the handling end of the elongated body, the surgical operation tool operable to perform a surgical manipulation of the surgical site; and
    a realization tool positioned along the elongated body and substantially adjacent to the realization tool, the realization tool operable to reflectively transmit (i) an image of the surgical site in one of a rendered or a non-rendered manner directly from the surgical site and directly to a user of the realization tool, (ii) a beam of light to the surgical site in one of a rendered or a non-rendered manner, or (iii) both, the realization tool selectively accessible before or after use of the surgical operation tool using the handle to (i) laterally shift the elongated body relative to the surgical site, (ii) change an angle of the elongated body relative to the surgical site, or (iii) laterally shift the elongated body relative to the surgical site and change an angle of the elongated body relative to the surgical site.

7. The medical instrument according to claim 6, wherein the realization tool includes a plurality of realization tools that are accessible with respect to the surgical operation tool by (i) laterally shifting the elongated body, (ii) laterally shifting the elongated body and rotating the elongated body 90°, (iii) laterally shifting the elongated body and rotating the elongated body 180°, and (iv) laterally shifting the elongated body and rotating the elongated body 270°.

8. The medical instrument according to claim 7, wherein the plurality of realization tools are positioned equidistant from a tip of the working end of the elongated body.

9. The medical instrument according to claim 6, wherein the realization tool has a degree of reflectivity to render the image of the surgical site or the beam of light to the surgical site with decreased clarity.

10. The medical instrument according to claim 6, wherein the realization tool includes a plurality of realization tools having different degrees of reflectivity to render the image of the surgical site or the beam of light to the surgical site with decreased clarity.

11. The medical instrument according to claim 6, wherein the realization tool has a configuration to render the image of the surgical site to be magnified or minimized or the beam of light to the surgical site to be focused or scattered.

12. The medical instrument according to claim 11, wherein the configuration of the realization tool includes at least one of a convex surface or a concave surface.

13. The medical instrument according to claim 6, wherein the realization tool includes a plurality of realization tools having a respective configuration operable to render the image of the surgical site to be magnified or minimized or the beam of light to the surgical site to be focused or scattered.

14. The medical instrument according to claim 13, wherein each configuration includes at least one of a convex surface or a concave surface.

15. The medical instrument according to claim 6, wherein the realization tool has a reflective surface that is parallel to or angled relative to an axis defined by the elongated body.

16. The medical instrument according to claim 6, further comprising:
a scale with units of measurement, the scale operable to permit sizing of an object and/or surface area, the scale positioned adjacent to the realization tool on the elongated body.

17. The medical instrument according to claim 16, wherein the scale is accessible with respect to the surgical operation tool by (i) laterally shifting the elongated body, or (ii) laterally shifting the elongated body and rotating the elongated body 45°.

18. The medical instrument according to claim 16, wherein the scale is accessible with respect to the realization tool by rotating the elongated body between 1° and 45°.

19. The medical instrument according to claim 6, wherein the realization tool is further operable to perform a dimensioning function, the dimensioning function providing a basis for a third dimension.

20. The medical instrument according to claim 6, wherein the surgical manipulation is a physical manipulation of a part of the surgical site, the physical manipulation being one of probing, shaving, ablating, burring, and biting.

* * * * *